US009232934B2

(12) United States Patent
Hershey et al.

(10) Patent No.: US 9,232,934 B2
(45) Date of Patent: Jan. 12, 2016

(54) SYSTEMS AND METHODS FOR COMMUNICATING ULTRASOUND PROBE LOCATION AND IMAGE INFORMATION

(71) Applicant: General Electric Company, Schenectady, NY (US)

(72) Inventors: John Erik Hershey, Ballston Lake, NY (US); Michael James Hartman, Clifton Park, NY (US); Michael Joseph Dell'Anno, Clifton Park, NY (US); Stanislava Soro, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 49 days.

(21) Appl. No.: 13/718,934

(22) Filed: Dec. 18, 2012

(65) Prior Publication Data
US 2014/0171797 A1  Jun. 19, 2014

Related U.S. Application Data (60) Provisional application No. 61/737,428, filed on Dec. 14, 2012.

(51) Int. Cl.
*A61B 8/00* (2006.01)
*G01S 15/89* (2006.01)
(Continued)

(52) U.S. Cl.
CPC .............. *A61B 8/56* (2013.01); *A61B 8/4245* (2013.01); *A61B 5/0022* (2013.01); *A61B 5/0073* (2013.01);
(Continued)

(58) Field of Classification Search
CPC ...... A61B 8/52; A61B 8/5238; A61B 8/4416; A61M 5/427; A61N 2005/1058
See application file for complete search history.

(56) References Cited

U.S. PATENT DOCUMENTS

| 5,368,032 A | 11/1994 | Cline et al. |
| 6,425,865 B1 | 7/2002 | Salcudean et al. |

(Continued)

FOREIGN PATENT DOCUMENTS

| GB | 1421575 A | 1/1976 |
| WO | 2007051261 A1 | 5/2007 |
| WO | 2011085469 A1 | 7/2011 |

OTHER PUBLICATIONS

Mitsuishi, M.; Warisawa, S, Remote ultrasound diagnostic system, Robotics and Automation, 2001. Proceedings 2001 ICRA. IEEE International Conference on 2001, pp. 1567-1574 vol. 2.

(Continued)

*Primary Examiner* — Mark Remaly
(74) *Attorney, Agent, or Firm* — The Small Patent Law Group LLC; Christopher R. Carroll (57) ABSTRACT

Systems and methods for communicating ultrasound probe location and image information are provided. One system includes an ultrasound device coupled with an ultrasound probe and configured to acquire ultrasound images of a subject. The ultrasound imaging system also includes at least one camera configured to acquire (i) scene information including ultrasound imagery of the ultrasound probe with the subject during an image scan and (ii) ancillary probe data. The ultrasound imaging system further includes a processor configured to receive the ultrasound images and the ancillary probe data and a multiplexing unit configured to receive (i) the ultrasound images and ancillary probe data from the processor and (ii) the scene information from the camera, wherein the multiplexing unit is further configured to associate in time the ultrasound images, ancillary probe data and scene information. The ultrasound imaging system additionally includes a communication device.

8 Claims, 7 Drawing Sheets

(51) Int. Cl.
*A61B 5/00* (2006.01)
*G01S 7/00* (2006.01)

(52) U.S. Cl.
CPC ............. *A61B 8/4254* (2013.01); *A61B 8/4263* (2013.01); *A61B 8/4472* (2013.01); *G01S 7/003* (2013.01); *G01S 15/899* (2013.01)

(56) References Cited

U.S. PATENT DOCUMENTS

| | | |
|---|---|---|
| 6,491,632 B1 | 12/2002 | Taylor |
| 6,569,097 B1 | 5/2003 | McMorrow et al. |
| 7,189,205 B2 | 3/2007 | McMorrow et al. |
| 7,331,925 B2 | 2/2008 | McMorrow et al. |
| 7,728,868 B2 | 6/2010 | Razzaque et al. |
| 8,055,329 B2 | 11/2011 | Kimchy et al. |
| 2002/0087080 A1* | 7/2002 | Slayton et al. ................ 600/459 |
| 2005/0256392 A1 | 11/2005 | Matory et al. |
| 2008/0214931 A1 | 9/2008 | Dickfeld et al. |
| 2009/0124906 A1 | 5/2009 | Caluser |
| 2010/0249592 A1* | 9/2010 | Langeland et al. ........... 600/443 |
| 2010/0268085 A1* | 10/2010 | Kruecker et al. ............. 600/443 |
| 2010/0286519 A1 | 11/2010 | Lee et al. |
| 2011/0015504 A1 | 1/2011 | Yoo |
| 2011/0112401 A1* | 5/2011 | Watanaba ..................... 600/443 |
| 2014/0171799 A1 | 6/2014 | Hershey et al. |

OTHER PUBLICATIONS

Philippe Arbeille, Arnaud Capri, Use of a Robotic Arm to Perform Remote Abdominal Telesonography, © American Roentgen Ray Society, Apr. 2007, vol. 188 No. 4 W317-W322.

Koizumi, N.; Warisawa, S., Construction Methodology for a Remote Ultrasound Diagnostic System, Robotics, IEEE Transactions on Jun. 2009, vol. 25 Issue:3, on pp. 522-538.

Cécilia Carron, Diagnosis based on remote ultrasound will soon be available, Mediacom, Jun. 2011.

* cited by examiner

SYSTEMS AND METHODS FOR COMMUNICATING ULTRASOUND PROBE LOCATION AND IMAGE INFORMATION

CROSS REFERENCE TO RELATED APPLICATIONS

This application claims priority to and the benefit of the filing date of U.S. Provisional Application No. 61/737,428 filed Dec. 14, 2012, the subject matter of which is herein incorporated by reference in its entirety.

BACKGROUND

Remote health care services, such as performing diagnostic imaging in remote locations that otherwise may not have adequate health care facilities, are increasing. This increase is due in part because in a typical centralized medical care system arrangement, the transportation of patients to a centralized facility takes time, which can result in treating patients later in a disease pathology, increasing cost and deteriorating outcomes.

Ultrasound or sonography has become an increasingly used tool for medical diagnosis. In conventional usage, the health care professional moves, orients, and presses the ultrasound probe over the regions of the patient's body as guided by the health care professional's experience and intuition. When an ultrasound examination is performed at a location remote to a specialist's location, such as by a remote health care practitioner (RHCP) in a medical dispensary remote from a major medical center such as a hospital, the protocol may require diagnosis and direction to be communicated to the remotely located health care professional administering the movement of the ultrasound probe. In these situations, it may not always be sufficiently clear where the ultrasound probe is located on the patient or the track that the probe has traversed.

Also, there are a number of components to the ultrasound probe's control that affect the ultrasound imagery and may aid in the diagnosis. These include the control movements of sliding, rotating, tilting, and compressing. Different operating conditions are also associated with these different control movements. For example, when the probe is slid, the angle of ultrasound beam energy should remain constant with respect to the body. This angle should also remain constant when the probe is rotated. Tilting of the probe is also performed while the probe is at a specific location over the body and may provide more accurate measurements. Compression of the tissue below the ultrasound transducer allows for better viewing of deeper structures and helps differentiate between structures. For example, veins are easily compressed by pressing the probe down, arteries less so, and nerves are essentially incompressible.

However, in remote health care applications, information regarding the ultrasound examination may not be properly communicated to another location, for example, where a specialist is located. Thus, the specialist located remotely from the point of examination may have difficulty associating the remotely acquired ultrasound imagery and probe control with the location on the patient's body corresponding to the imagery.

SUMMARY

In one embodiment, an ultrasound imaging system is provided that includes an ultrasound device coupled with an ultrasound probe and configured to acquire ultrasound images of a subject. The ultrasound imaging system also includes at least one camera configured to acquire (i) scene information including ultrasound imagery of the ultrasound probe with the subject during an image scan and (ii) ancillary probe data. The ultrasound imaging system further includes a processor configured to receive the ultrasound images acquired by the ultrasound device and the ancillary probe data acquired by the camera and a multiplexing unit configured to receive (i) the ultrasound images and ancillary probe data from the processor and (ii) the scene information from the camera, wherein the multiplexing unit is further configured to associate in time the ultrasound images, ancillary probe data and scene information. The ultrasound imaging system additionally includes a communication device coupled to the multiplexing unit and configured to communicate the time associated ultrasound images, ancillary probe data and scene information to a remote device.

In another embodiment, an ultrasound imaging system is provided that includes an ultrasound device coupled with an ultrasound probe and configured to acquire ultrasound images of a subject during an ultrasound examination. The ultrasound imaging system further includes at least one camera configured to acquire photographic imagery of the ultrasound probe with the subject during the ultrasound examination and a multiplexing unit configured to associate in time the ultrasound images, the photographic imagery and ancillary probe data. The ultrasound imaging system also includes a communication device coupled to the multiplexing unit and configured to communicate the time associated ultrasound images, photographic imagery and ancillary probe data to a remote device.

In yet another embodiment, a method for communicating ultrasound information is provided. The method includes obtaining ultrasound imagery for a subject, wherein the ultrasound imagery is acquired by an ultrasound probe during an ultrasound examination. The method further includes obtaining photographic scene imagery of the ultrasound probe with the subject during the ultrasound examination, wherein the photographic imagery acquired by a camera. The method also includes obtaining ancillary probe data from at least one of the ultrasound probe or the camera, multiplexing in time the ultrasound imagery with the photographic scene imagery and the ancillary probe data, and communicating the time multiplexed ultrasound imagery, photographic scene imagery and ancillary probe data to a remote device.

DETAILED DESCRIPTION

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and method for conducting or performing an ultrasound examination, photographing the examination, and associating in time, for transmission, the ultrasound imagery with the photographic scene imagery and any ultrasound probe ancillary data (e.g., probe angle, tilt, orientation or compression). For example, in one embodiment, at least one camera may be used to acquire (i) scene information including ultrasound imagery of the ultrasound probe with the subject during an image scan and (ii) ancillary probe data (in some embodiments the ancillary probe data may be alternatively or optionally acquired by a separate device). In various embodiments, ultrasound images acquired from an ultrasound probe along with the scene information from the camera and ancillary probe data are multiplexed or associated in time for transmission from the examination location to a location remote therefrom, such as a specialist's location.

At least one technical effect of various embodiments is an improved association of remotely acquired ultrasound imagery and probe control with the location on the patient's body corresponding to the imagery.

Various embodiments provide systems and methods for communicating information relating to an ultrasound scan from one location to another remote location. In one embodiment, an imaging system is provided that communicates information, such as diagnostic images (e.g., ultrasound images), from one location (e.g., a patient examination site) to another location (e.g., a hospital remote from the examination site) along with probe location information, as well as ancillary probe data, which may be communicated over one or more communication channels. It should be noted that the images may be, for example, a streaming series or sequence of images over one or more communication channels. In one embodiment, for example, a remote health care practitioner (RHCP) may be guided by a specialist using the communicated information. The communicated information is multiplexed, correlated, associated or synchronized in various embodiments.

Figure 1:
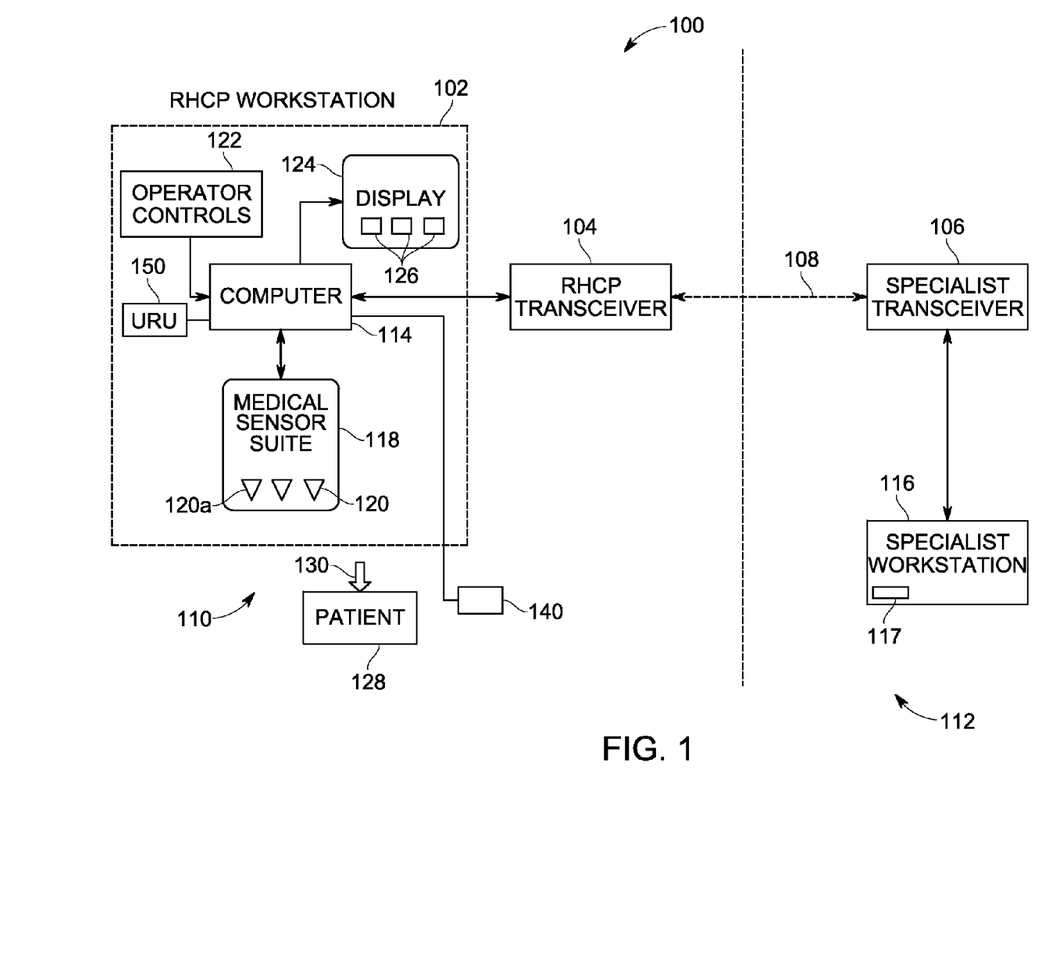
FIG. 1 is a schematic block diagram of a medical data communication system formed in accordance with an embodiment.

FIG. 1 is a schematic block diagram of a medical data communication system 100 for communicating image data, along with images (e.g., photographic images) of an exam and optionally ancillary probe data in accordance with various embodiments. The system 100 is generally configured to acquire medical images, such as ultrasound imagery (e.g., a plurality of ultrasound images over time) at the RHCP's location (as well as probe location information acquired, for example, by one or more cameras) and transmit the ultrasound imagery and probe location information (along with optional ancillary probe data) to, for example, a remotely located specialist for viewing, consultation and/or guidance, which may include providing feedback. The system 100 includes an RHCP workstation 102 that allows acquisition of image data (and probe location information, as well as ancillary probe data) and interface with a user or operator, such as the RHCP. It should be noted that although various embodiments are described in connection with communicating ultrasound data, the various embodiments may be used to communicate other types of medical and non-medical image data, such as other types of medical images, diagnostic audio, electrocardiogram (ECG) and other physiological waveforms, which may be communicated in a streaming manner.

The system 100 includes an RHCP transceiver 104 that communicates with a remote transceiver, which in the illustrated embodiment is a specialist transceiver 106 (e.g., a transceiver located at a location of a specialist). The transceivers 104, 106 communicate over or form a communication link 108, which may include one or more communication channels (e.g., cellular network communication channels). Accordingly, the communication link 108 provides bi-directional or two-way communication between a first location 110 and a second location 112, which may be an examination location and a specialist location remote therefrom (e.g., miles away), respectively, in one embodiment.

With respect to the first location 110 where the image data is acquired and processed, the RHCP workstation 102 includes a processor, which is illustrated as a computer 114. The computer 114 is coupled to the RHCP transceiver 104 to allow communication between the computer 114 and another workstation at the second location 112, illustrated as a specialist workstation 116, via the specialist transceiver 106. It should be noted that the RHCP transceiver 104 and the specialist transceiver 106 may form part of or be separate from the RHCP workstation 102 and the specialist workstation 116, respectively. It also should be noted that the workstations 102 and 116 may be any types of workstations usable by different types of operators (and in some embodiments, may be electronic tablet devices, notebook computers, cellular phones, etc.). The specialist workstation 116 may be, for example, a data server where multiple workstations may be connected and interacting with the computer 114 at the patient location, such as the RHCP workstation 102.

The computer 114 is also connected to one or more medical devices 120 illustrated as a medical sensor suite 118. The medical devices 120 may be removably and operatively coupled to an interface (now shown) of the RHCP workstation 102 to allow communication therebetween. The medical sensor suite 118 may include a plurality of different types or kinds of medical devices, such as plurality of different types of medical imaging probes that may be used for different imaging applications. In one embodiment, the medical device 120a is an ultrasound imaging apparatus that may be used to image a patient 128 or a portion of the patient 128.

The computer 114 is also coupled to a user input 122 that includes one or more user controls (e.g., keyboard, mouse, touchpad or touchscreen) for interfacing or interacting with the RHCP workstation 102. The computer 114 is also coupled to a display 124, which may be configured to display one or more ultrasound images 126, such as in a time sequence or loop of images, also known as a cine loop. In operation, a user is able to control the display of the images 126 on the display 124 using the user input 122, for example, controlling the particular display settings. The user input 122 may also allow a user to control the acquisition of the image data used to generate the images 126, such as the image acquisition settings or controls. In one embodiment, the user input 122 allows control of the ultrasound imaging apparatus 120a.

The ultrasound imaging apparatus 120a is configured to acquire ultrasound image data that may be processed by the ultrasound imaging apparatus 120a or the RHCP workstation 102 to generate one or more images (e.g., 2D, 3D or 4D images) of a region of interest, for example an anatomy of interest, of a subject, such as the patient 128. The ultrasound imaging apparatus 120a or the RHCP workstation 102 generates one or more images by reconstructing imaging data acquired by the ultrasound imaging apparatus 120a. It should be noted that as used herein, imaging data and image data both generally refer to data that may be used to reconstruct an image.

In one embodiment, the imaging data is acquired with an imaging probe 130. The imaging probe 130 may be a handheld ultrasound imaging probe. Alternatively, the imaging probe 130 may be an infrared-optical tomography probe. The imaging probe 130 may be any suitable probe for acquiring ultrasound images in another embodiment. The imaging probe 130 may be mechanically coupled to the ultrasound imaging apparatus 120a. Alternatively or optionally, the imaging probe 130 may be in wireless communication with the ultrasound imaging apparatus 120a. In still other embodiments, the imaging probe 130 is alternatively or optionally coupled to the RHCP workstation 102.

The computer 114 is further coupled to a camera 140, which in one embodiment, is a digital camera. For example, the camera 140 may communicate images with probe location information (and optionally ancillary probe data) for associating in time the location of the imaging probe 130 with one or more corresponding image frames acquired during an image scan by the ultrasound imaging apparatus 120a, and which are communicated to a remote location. For example, the camera 140 in various embodiments is configured to acquire "scene information", which in various embodiments is one or more (e.g., a series of) digital pictures of the examination scene (which may indicate the position of the probe, such as showing sliding, rotating or tilting of the probe or compression by the probe), including the patient 128 and the probe 130 being used to acquire the ultrasound image data. The camera 140 may acquire digital pictures periodically (e.g., every 3, 5, 10 or 30 seconds) during the ultrasound scan. The camera 140 may be any suitable digital camera, for example, a camera having a defined minimum resolution level (e.g., 5 mega-pixels) and optionally optical or digital zoom capabilities. Is some embodiments, the camera 140 also allows for storage therein of the acquired scene images.

In operation, data acquired by the ultrasound imaging apparatus 120a and the camera 140 is accessible and may be communicated between the first location 110 and the second location 112 using the transceivers 104, 106. It should be noted that the transceivers 104, 106 may be configured to communicate using any suitable communication protocol, such as a suitable wireless communication protocol, for example cellular 3G communication protocols. Using this arrangement, data from the computer 114 at the RHCP workstation 102 may be transmitted to a specialist at the specialist workstation 116 and data sent from the specialist may be received at the RHCP workstation 102.

Figure 2:
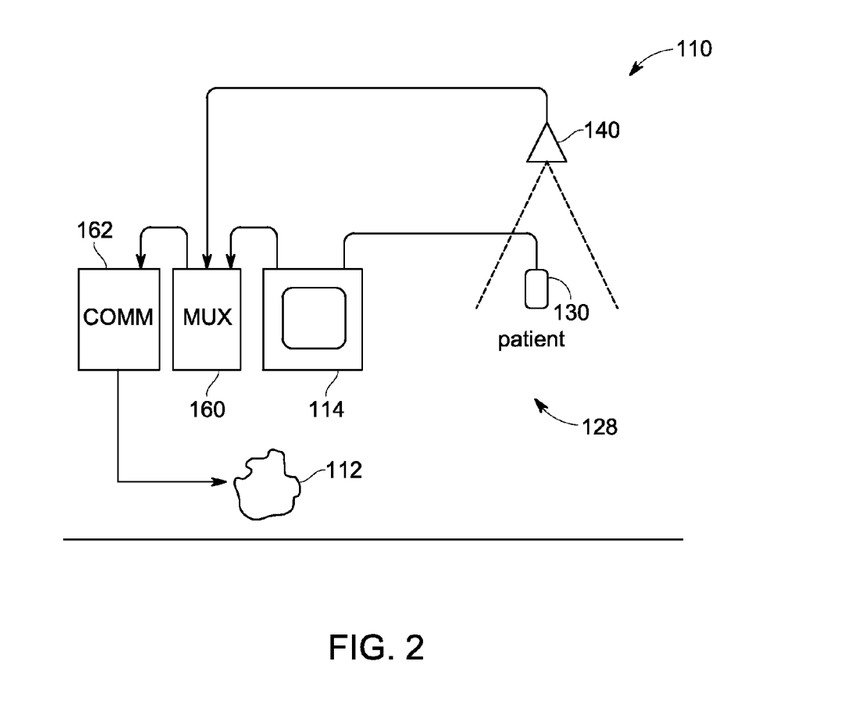
FIG. 2 is a diagram illustrating a camera and communication arrangement within the medical data communication system of FIG. 1.

Various embodiments provide for acquiring and communicating probe location information correlated or synchronized (e.g., synchronized in time) with the acquired scene information and optionally the ancillary probe data. For example, as shown in FIG. 2, which illustrates the first location 110, various embodiments acquire information to allow a remotely located specialist to associate the ultrasound probe's position and track on an examined patient. The system 100 in various embodiments provides a multiplexed association scheme to enable this association. It should be noted that FIG. 2 illustrates only some of the components of the system 100 for ease of illustration.

The patient 128 is shown examined using the ultrasound probe 130. This data is used to form one or more ultrasound imagery frames by a processor, such as the computer 114, which may also perform a local image display function.

The camera 140 (e.g., a digital camera), which may be a scene imagery camera views the patient 128 and the ultrasound probe 130 during the ultrasound examination. The camera 140 may also have sufficient resolution and be so positioned with respect to the patient 128 and the ultrasound probe 130 that that the captured scene imagery is sufficient for discerning not only the probe's position on the patient 128, but also ancillary probe data, such as the probe orientation angle with respect to a reference line on the patient (e.g., an imaginary or virtual line) and the probe's tilt angle with respect to the patient's surface, and/or the probe pressure or compression exerted on the patient 128 thereby compressing the patient's tissue directly under the probe 130. The ancillary probe data may be determined using image processing techniques that identify the objects within the images and correlate the object positions. In other embodiments, a user may visually determine the ancillary probe data, as well as the probe location.

In some situations, ancillary probe data, such as the probe orientation angle and tilt angle and compression may be measured by the probe 130. In particular, the location of the probe may be determined or supplemented using other devices. For example, probes with sensors that allow a determination of the magnetic orientation of the device may be used. As another example, accelerometers may be used in connection with the probe 130, for example, a three-axis accelerometer, a gyroscope, such as a three-axis gyroscope, or the like that determines the x, y, and z coordinates of the probe 130. As still another example, local location mechanisms or GPS (or the like) may be used. Thus, in some embodiments the probe 130 may include a sensor coupled therewith (e.g., a differential sensor). The sensor may be externally coupled to the probe 130 or may be formed integrally with and positioned in a housing of the probe 130 in other embodiments. The tracking device may receive and transmit signals indicative of a position thereof and is used to acquire positional data of the probe 130. For example, the sensor may determine a position and an orientation of the probe 130. Other position sensing devices may be used, for example, optical, ultrasonic, or electro-magnetic position detection systems.

In some cases, other ancillary probe data, such as probe compression may be estimated by techniques based on sequential ultrasound image frame cross-correlations by, for example, inferring differential compression by changes in the dimensions of veins within the image as probe pressure is increased.

It should be noted that the probe location information and/or scene information also may be acquired using different suitable techniques. For example, this information may be acquired as described in co-pending application entitled "Systems and Methods for Providing Ultrasound Probe Location and Image Information" having U.S. application Ser. No. 13/718,762, which is commonly owned.

In various embodiments, the ultrasound imagery and any ancillary probe data are sent from the computer 114 to a multiplexing (mux) unit 160 which also receives the time associated scene imagery from the camera 140 (e.g., time stamped information). The multiplexing unit 150 creates an association between the ultrasound imagery frames and the scene imagery frames and any time associated ancillary probe data and transfers this data to a communication device (COMM) 162 that sends the data to the remote specialist's location 112.

It should be noted that the multiplexing unit 160 may use different methods and techniques to create data associations and is not limited to any specific method or the methods described herein. For example, in one embodiment, the multiplexing unit 160 assigns and/or affixes time tags to the different imagery data and any ancillary probe data and creates a table with time tags to associate the individual ultrasound imagery frames, the scene imagery frames, and any associated ancillary probe data. At the remote specialist's location 112, the synchronization between the ultrasound imagery frames, the scene imagery frames, and any associated ancillary probe data may be established by using the time tags.

In another embodiment, an ultrasound imagery frame is embedded with the time synchronized scene imagery frame and any time synchronized ancillary probe data into the same data packet which is sent to the specialist's location 112. In this embodiment, each of the data packets may also include a time stamp that identifies the time the packet fields within the data packet were produced. This will then allow the data in the data packets to be displayed and studied in the order in which the data packets were produced.

Figure 3:
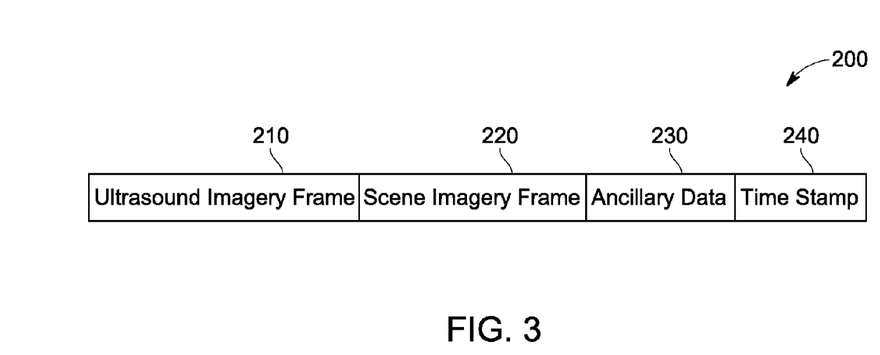
FIG. 3 is a block diagram of a data packet in accordance with various embodiments.

For example, an exemplary data packet structure is illustrated in FIG. 3. The data packet 200 is composed of field 210 containing an ultrasound imagery frame, field 220 containing the time associated scene imagery frame, field 230 containing any time associated probe ancillary data, and optional field 240 containing the time stamp. Thus, the data packet 200 may include control information and data (which may be referred to as the payload). Accordingly, the data within the different fields may be data that was acquired at the same time and synchronized based on time stamps. The data packets 200 may be generated, communicated and processed using techniques suitable for transmitting such data, for example, medical data.

It should be noted that variations and modifications are contemplated. For example, data compression may be used between successive imagery frames, and any successive ancillary probe data. In particular, sequential scene imagery frames may be highly correlated and compressible, such as compression of successive differences.

In various embodiments, ultrasound data registration is provided, for example, by communicating position information for the probe 130 (e.g., scene images showing the probe 130 in combination with or in contact with the patient 128) to the computer 114 by one or more cameras 140 and the location of the probe is then referenced to the patient's body along with associating any ancillary probe data. For example, the information from the camera(s) 140 and probe 130 may be time stamped with the time stamp information then used to identify and correlate the image data acquired by the probe 130 to the corresponding location information and any ancillary probe data, such that the information is synchronized in time.

In various embodiments, the multiplexing unit 160 reserves locations within the multiplexing process to allow portions of the data to align properly with the particular time segment. For example, the communicated information is synchronized or time stamp or synchronizing information is provided to ensure that the ultrasound imagery (e.g., ultrasound image frame) is synchronized in time with the image of the patient to allow correlation or identification of the probe location or orientation (along with other ancillary probe data) with the ultrasound imagery.

Figure 4:
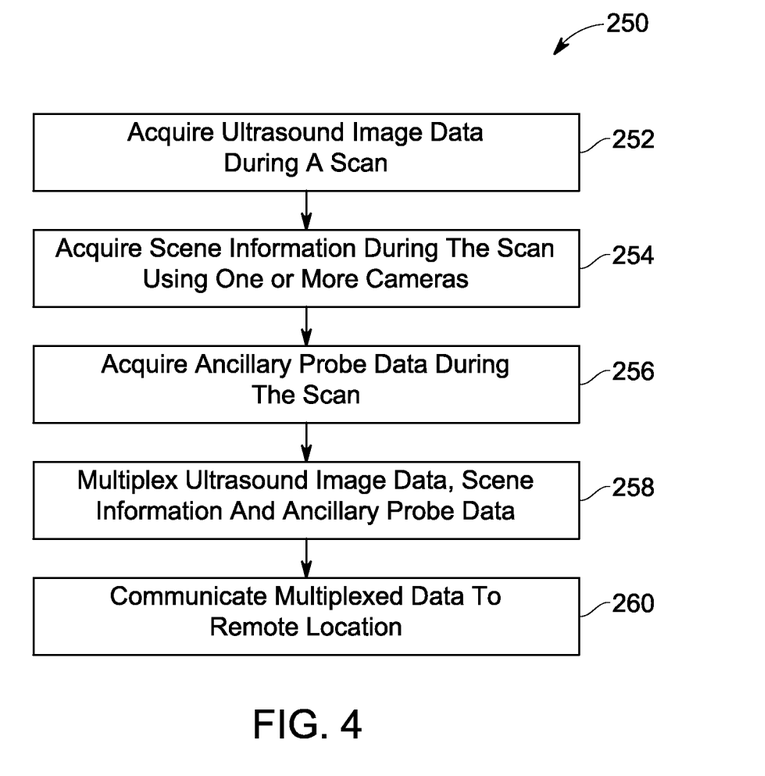
FIG. 4 is a flowchart of a method for generating and communicating probe location information with ultrasound image data in accordance with various embodiments.

A flowchart of a method 250 in accordance with various embodiments for generating and communicating probe location information (and optionally ancillary probe data) synchronized with ultrasound image data is shown in FIG. 4. The method 250 allows for the determination of the location of the probe relative to the patient's body (and any ancillary probe data) to be communicated to a remote location with the scene information or scene image data such that the probe location information corresponding to frames of ultrasound data are correlated or synchronized. Thus, the image scene of the patient is time synchronized with the acquired probe images and multiplexed into data packets to allow transmission to a remote location where the data may be displayed to a user in a time associated manner.

The method 250 includes acquiring at 252 ultrasound image data during a scan, for example, an ultrasound examination of a patient. The ultrasound image data may include acquiring ultrasound images using a determined scan protocol. During the scan, the operator may move (e.g., rotate or translate) the probe to acquire different views or image frames of a region of interest, which may be processed to generate ultrasound imagery.

The method 250 also includes acquiring scene information during the scan at 254. The scene information in various embodiments provides probe location information during the scan showing the probe in relation to the patient during the scan. In various embodiments, the probe location information is acquired using one or more digital cameras (and optionally the probe or a device coupled to the probe). For example, during the scan, time stamped images of the patient and probe are acquired and stored. The time stamping of these digital scene images allows for correlation to the ultrasound image data acquired at 252.

The method 250 further includes acquiring ancillary probe data during the scan at 256. As described in more detail herein, the ancillary probe data may be acquired or determined using the scene information and alternatively or optionally using the probe or a device coupled with the probe. Thus, while the scene information provides the location of the probe relative to the patient during the scan, the ancillary probe data may provide more information regarding the position (e.g., tilt angle, orientation angle or rotation) of the probe or the operating state or characteristics of the probe (e.g., probe compression on the patient). It should be noted that step 256 is optionally performed in various embodiments.

The method 250 additionally includes multiplexing the ultrasound image data, scene information and ancillary probe data at 258. In particular, various embodiments provide a multiplexed association scheme such that, for example, a remotely located specialist may use to associate the position of the ultrasound probe and track on an examined patient. For example, data packets are generated that include multiplexed data, which may include ultrasound imagery, image scenes (e.g., photographic images of the examination area including the probe) and ancillary probe data. In one embodiment, each data packet corresponds to a time stamped event during the ultrasound examination. For example, the multiplexing sequence may include reserved locations for the portions of data (e.g., the different types of data or information) for each of a plurality of time segments to ensure data associations such that data packets received at the remote location, when processed, can identify, for example, scene information and ancillary probe data corresponding to particular image frames. Thus, in various embodiments, data packets are created at the location of the examination, such as by populating the packets with data that is associated by the multiplexing in some embodiments. The data packets are then communicated to another location, for example, to a specialist at a remote location. The system at the location of the specialist may parse the received packets to extract data in a plurality of data fields as described in more detail herein.

It should be noted that the data packets may correspond to data for a currently performed ultrasound examination or for a previously performed ultrasound examination.

The method 250 also includes communicating the multiplexed data to a remote location at 260, for example, from the examination location to a location of the specialist. The communication may be performed using different communication standards or protocols. The communicated multiplexed data may then be processed such that, for example, the specialist located remotely from the point of examination can better associate the remotely acquired ultrasound imagery and probe control with the location on the patient's body corresponding to the ultrasound imagery. For example, photographic scene images synchronized with ultrasound imagery and optionally additional ancillary probe information may be displayed using the multiplexed data.

In various embodiments, the display at, for example, the specialist location may also display a three-dimensional (3D) model (e.g., 3D representation) of the patient. In one embodiment, if the image data is of a poor or lower quality (e.g., the specialist is unable to determine the location of probe), the display at the specialist workstation 116 may additionally, optionally or alternatively display a 3D body model with the probe location overlaid on the model. For example, as part of the data communicated from the RHCP workstation 102, respective coordinates of the probe location and orientation can be sent and associated on the 3D body model.

Figure 5:
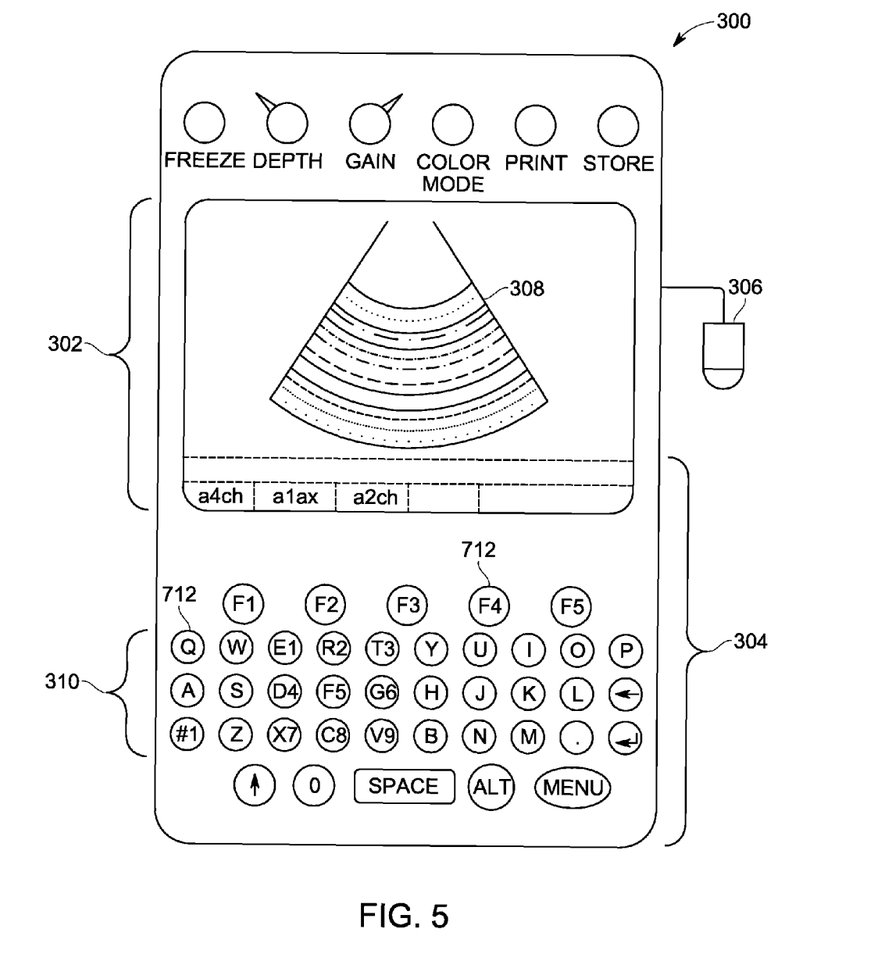
FIG. 5 illustrates a hand carried or pocket-sized ultrasound imaging system formed in accordance with an embodiment.

The various embodiments may be implemented in connection with different imaging systems, such as different ultrasound imaging systems. For example, FIG. 5 illustrates a hand carried or pocket-sized ultrasound imaging system 300 (which may be embodied as part of the system 100 shown in FIG. 1). The ultrasound imaging system 300 may be configured to operate and multiplex images and probe location information (as well as ancillary probe information) as described in the method 250 (shown in FIG. 4) for communication to a remote location. The ultrasound imaging system 300 has a display 302 and a user interface 304 formed in a single unit. By way of example, the ultrasound imaging system 300 may be approximately two inches wide, approximately four inches in length, and approximately half an inch in depth. The ultrasound imaging system may weigh approximately three ounces. The ultrasound imaging system 700 generally includes the display 302 and the user interface 304, which may or may not include a keyboard-type interface or touch screen and an input/output (I/O) port for connection to a scanning device, for example, an ultrasound probe 306. The display 302 may be, for example, a 320×320 pixel color LCD display on which a medical image 308 or series of medical images 308 may be displayed. A typewriter-like keyboard 310 of buttons 312 may optionally be included in the user interface 304.

The probe 306 may be coupled to the system 300 with wires, cable, or the like. Alternatively, the probe 306 may be physically or mechanically disconnected from the system 300. The probe 306 may wirelessly transmit acquired ultrasound data to the system 300 directly or through an access point device (not shown), such as an antenna disposed within the system 300.

Figure 6:
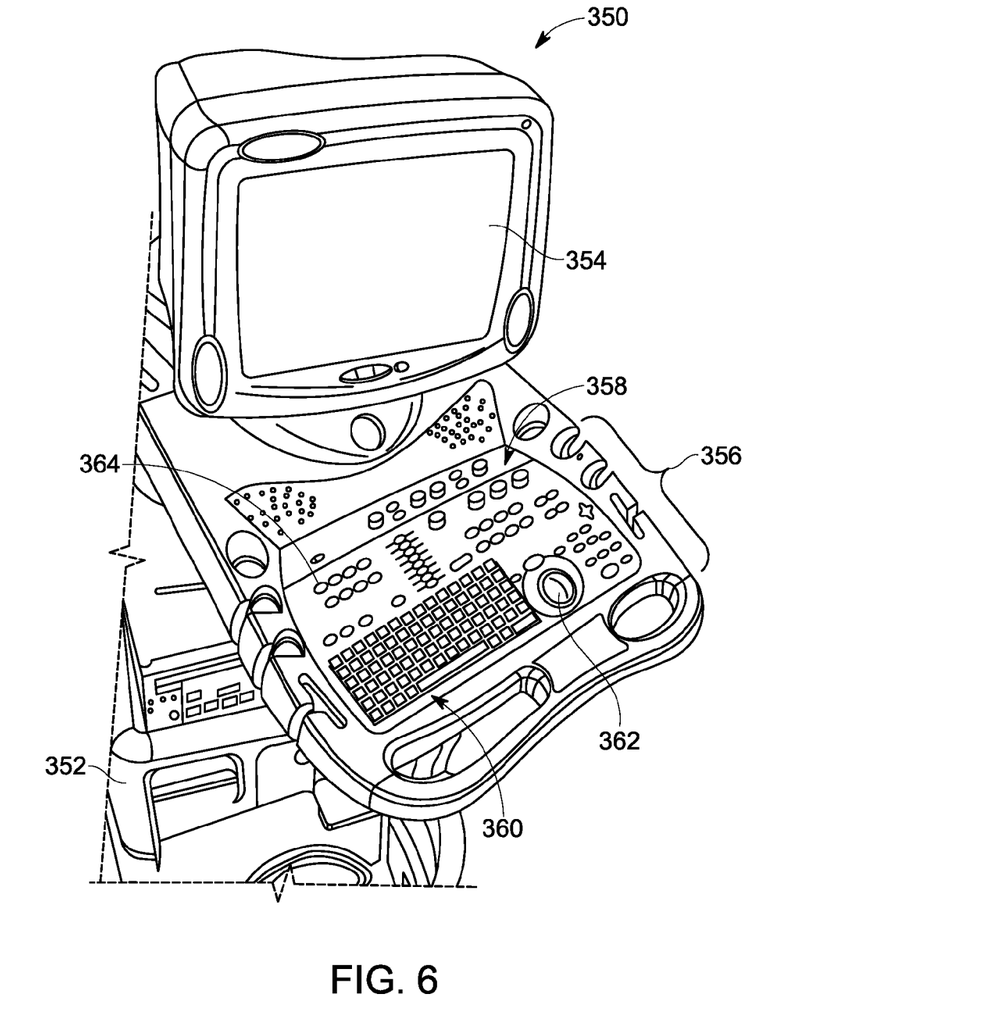
FIG. 6 illustrates an ultrasound imaging system formed in accordance with an embodiment and provided on a moveable base.

FIG. 6 illustrates an ultrasound imaging system 350 (which may be embodied as part of the system 100) provided on a moveable base 352. The ultrasound imaging system 350 may be configured to operate as described in the method 250 (shown in FIG. 4). A display 354 and a user interface 356 are provided and it should be understood that the display 354 may be separate or separable from the user interface 356. The user interface 356 may optionally be a touchscreen, allowing an operator to select options by touching displayed graphics, icons, and the like.

The user interface 356 also includes control buttons 358 that may be used to control the system 350 as desired or needed, and/or as typically provided. The user interface 356 provides multiple interface options that the user may physically manipulate to interact with ultrasound data and other data that may be displayed, as well as to input information and set and change scanning parameters and viewing angles, etc. For example, a keyboard 360, trackball 362, and/or other controls 364 may be provided. One or more probes (such as the probe 130 shown in FIG. 1) may be communicatively coupled with the system 350 to transmit acquired ultrasound data to the system 350.

Figure 7:
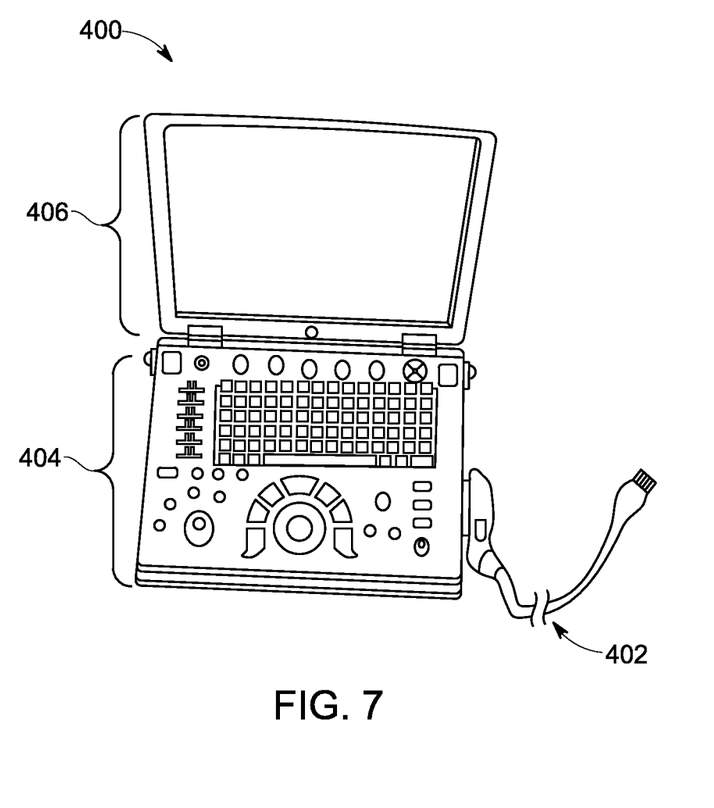
FIG. 7 illustrates a 3D-capable miniaturized ultrasound system formed in accordance with an embodiment.

FIG. 7 illustrates a 3D-capable miniaturized ultrasound system 400 (which may be embodied as part of the system 100). The ultrasound imaging system 400 may be configured to operate as described in the method 250 (shown in FIG. 4). The ultrasound imaging system 400 has a probe 402 that may be configured to acquire 3D ultrasonic data or multi-plane ultrasonic data. A user interface 404 including an integrated display 806 is provided to receive commands from an operator. As used herein, "miniaturized" means that the ultrasound system 400 is a handheld or hand-carried device or is configured to be carried in a person's hand, pocket, briefcase-sized case, or backpack. For example, the ultrasound system 400 may be a hand-carried device having a size of a typical laptop computer. The ultrasound system 400 is easily portable by the operator, such as in locations remote from a hospital or major health care facility. The integrated display 406 (e.g., an internal display) is configured to display, for example, one or more medical images.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, flash drive, jump drive, USB drive and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the described subject matter without departing from their scope. While the dimensions and types of materials described herein are intended to define the parameters of the various embodiments, the embodiments are by no means limiting and are exemplary embodiments. Many other embodiments will be apparent to one of ordinary skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable one of ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An ultrasound imaging system, comprising:
   an ultrasound imaging apparatus including an ultrasound probe and configured to acquire ultrasound images of a subject;
   at least one camera configured to acquire (i) scene information including ultrasound imagery of the ultrasound probe with the subject during an image scan;
   a processor configured to receive the ultrasound images acquired by the ultrasound imaging apparatus and the scene information acquired by the camera, the processor configured to determine ancillary probe data based on at least one of i) image processing of the scene information or ii) probe positioned data acquired by a tracking device;
   a multiplexing unit configured to receive (i) the ultrasound images and ancillary probe data from the processor and (ii) the scene information from the camera, the multiplexing unit further configured to associate in time the ultrasound images, ancillary probe data and scene information;
   a remote device; and
   a transceiver coupled to the multiplexing unit and configured to communicate the time associated ultrasound images, ancillary probe data and scene information to the remote device for display in a time associated manner, wherein the remote device includes a display configured to display the ancillary probe data to the user to provide information regarding at least one of i) a position or ii) an operating state, of the probe.

2. The ultrasound imaging system of claim 1, wherein the camera is a digital camera having at least one of (i) a resolution or (ii) a positioning with respect to the subject and the ultrasound probe to acquire image information of a position of the ultrasound probe on the patient and the ancillary probe data.

3. The ultrasound imaging system of claim 1, wherein the ancillary probe data comprises at least one of a probe orientation angle of the ultrasound probe with respect to a reference line on the subject or a tilt angle of the ultrasound probe with respect to a surface of the subject, the remote device configured to display the ancillary probe data.

4. The ultrasound imaging system of claim 1, wherein the ancillary probe data comprises one of a pressure or compression of the ultrasound probe on the subject, the remote device configured to display the ancillary probe data.

5. The ultrasound imaging system of claim 1, wherein the ultrasound images, ancillary probe data and scene information include time tags and wherein the remote device comprises a processor configured to time synchronize the ultrasound images, ancillary probe data and scene information using the time tags, wherein the remote device comprises a display configured to display the ultrasound images, ancillary probe data and scene information time synchronized using the time tags.

6. The ultrasound imaging system of claim 1, wherein the transceiver is configured to embed an ultrasound image frame of the ultrasound images with a time synchronized scene imagery frame of the scene information and time synchronized ancillary probe data into a single data packet communicated to the remote device for display.

7. The ultrasound imaging system of claim 6, wherein the data packet comprises a time stamp identifying a time that packet fields in the data packet were created.

8. The ultrasound imaging system of claim 1, wherein the processor is configured to perform compression between successive imagery frames of the scene information and successive ancillary probe data.

* * * * *